(12) United States Patent
Sauer (10) Patent No.: US 10,893,861 B2
(45) Date of Patent: Jan. 19, 2021

(54) SURGICAL PORT FOR STAY SUTURES

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 15/626,741

(22) Filed: Jun. 19, 2017

(65) Prior Publication Data

US 2018/0070938 A1 Mar. 15, 2018

Related U.S. Application Data

(60) Provisional application No. 62/351,567, filed on Jun. 17, 2016.

(51) Int. Cl.
*A61B 17/02* (2006.01)
*A61B 17/04* (2006.01)
*A61B 17/34* (2006.01)
*A61B 17/06* (2006.01)

(52) U.S. Cl.
CPC ...... *A61B 17/0469* (2013.01); *A61B 17/0482* (2013.01); *A61B 17/0485* (2013.01); *A61B 17/06061* (2013.01); *A61B 17/3417* (2013.01); *A61B 17/3423* (2013.01); *A61B 17/3496* (2013.01); *A61B 2017/0225* (2013.01); *A61B 2017/3445* (2013.01); *A61B 2017/3447* (2013.01); *A61B 2017/3454* (2013.01)

(58) Field of Classification Search
CPC ......... A61B 17/0401; A61B 2017/0446–0456; A61B 2017/0459–0461; A61B 2017/0403–0408; A61B 17/3417; A61B 17/3423; A61B 17/3496; A61B 17/3445; A61B 2017/3445; A61B 2017/3454; A61B 17/0469; A61B 17/0482; A61B 17/0485; A61B 17/06061; A61B 1/32; A61B 17/02
See application file for complete search history.

(56) References Cited

U.S. PATENT DOCUMENTS

| | | | | |
|---|---|---|---|---|
| 4,185,636 | A | * | 1/1980 | Gabbay ............ A61B 17/06061 606/148 |
| 5,616,131 | A | * | 4/1997 | Sauer ................. A61B 17/0469 604/174 |
| 5,972,030 | A | * | 10/1999 | Garrison .......... A61B 17/00234 623/2.11 |
| 6,010,531 | A | * | 1/2000 | Donlon ............ A61B 17/00234 623/2.1 |

(Continued)

OTHER PUBLICATIONS

Mar. 27, 2015 Journal; Bajpai M, The Percutaneous 'Pick and Fix' Suture: A Surrogate Port for Paediatric Laparoscopic Procedures; See pp. 1-5, in vol. 2, from issue 4, as published by Austin J. Gastroenterol.

*Primary Examiner* — Eduardo C Robert
*Assistant Examiner* — Michelle C Eckman
(74) *Attorney, Agent, or Firm* — Christopher B. Miller; David J. Gervasi (57) ABSTRACT

A surgical port is disclosed. The surgical port has a multi-level flange defining one or more suture channels therethrough. Adjacent levels of the multi-level flange are configured to pinch one or more sutures placed therebetween. The surgical port also has a cannular frame defining one or more cannular channels in communication with the one or more suture channels.

12 Claims, 9 Drawing Sheets

(56) References Cited

U.S. PATENT DOCUMENTS

| | | | |
|---|---|---|---|
| 7,029,481 B1* | 4/2006 | Burdulis, Jr. | A61B 17/0469 606/144 |
| 7,993,355 B2 | 8/2011 | Morris | |
| 8,123,806 B1* | 2/2012 | Hoof | A61B 17/0483 623/13.13 |
| 2001/0008971 A1* | 7/2001 | Schwartz | A61B 17/0401 606/232 |
| 2003/0195562 A1* | 10/2003 | Collier | A61B 17/0401 606/232 |
| 2004/0073233 A1* | 4/2004 | Jannot | A61B 17/06061 606/148 |
| 2005/0065535 A1* | 3/2005 | Morris | A61B 17/0469 606/148 |
| 2005/0149120 A1* | 7/2005 | Collier | A61B 17/0401 606/232 |
| 2005/0171404 A1* | 8/2005 | Mische | A61B 17/0293 600/231 |
| 2006/0064125 A1* | 3/2006 | Henderson | A61B 17/02 606/215 |
| 2006/0167479 A1* | 7/2006 | Morris | A61B 17/0469 606/148 |
| 2007/0073342 A1* | 3/2007 | Stone | A61B 17/0057 606/232 |
| 2007/0088277 A1* | 4/2007 | McGinley | A61B 17/3462 604/167.01 |
| 2007/0156023 A1* | 7/2007 | Frasier | A61B 17/0293 600/206 |
| 2008/0097527 A1* | 4/2008 | Lim | A61B 17/0487 606/232 |
| 2008/0294123 A1* | 11/2008 | Lunn | A61B 17/3462 604/256 |
| 2008/0306510 A1* | 12/2008 | Stchur | A61B 17/0401 606/232 |
| 2009/0005794 A1* | 1/2009 | Lowry | A61B 17/0206 606/148 |
| 2010/0191261 A1* | 7/2010 | Carter | A61B 17/06061 606/150 |
| 2010/0198019 A1* | 8/2010 | Bergeron | A61B 17/06061 600/235 |
| 2010/0210912 A1* | 8/2010 | Bettuchi | A61B 17/06061 600/201 |
| 2010/0234688 A1* | 9/2010 | Carter | A61B 17/06061 600/208 |
| 2010/0249810 A1* | 9/2010 | Taylor | A61B 17/3421 606/148 |
| 2011/0046449 A1* | 2/2011 | Minnelli | A61B 1/00128 600/205 |
| 2012/0035623 A1* | 2/2012 | Bagaoisan | A61B 17/0057 606/144 |
| 2012/0053623 A1* | 3/2012 | Sojka | A61B 17/0401 606/232 |
| 2012/0316593 A1* | 12/2012 | Kim | A61B 17/0218 606/185 |
| 2013/0102876 A1* | 4/2013 | Limon | A61F 5/0056 600/409 |
| 2013/0158600 A1* | 6/2013 | Conklin | A61B 17/0401 606/232 |
| 2013/0261663 A1* | 10/2013 | Bittenson | A61B 17/0401 606/232 |
| 2013/0282028 A1* | 10/2013 | Conklin | A61B 17/0487 606/144 |
| 2014/0074123 A1* | 3/2014 | Voss | A61B 17/0057 606/144 |
| 2014/0074124 A1* | 3/2014 | Voss | A61B 17/0057 606/144 |
| 2014/0074126 A1* | 3/2014 | Voss | A61B 17/0057 606/148 |
| 2014/0257314 A1* | 9/2014 | Brown | A61B 17/0401 606/98 |
| 2014/0316442 A1* | 10/2014 | Van Loenen | A61B 17/0469 606/144 |
| 2014/0324099 A1* | 10/2014 | Hernandez | A61B 17/0401 606/232 |
| 2015/0216514 A1* | 8/2015 | Weisbrod | A61B 17/0401 606/232 |
| 2015/0240852 A1* | 8/2015 | Eaves, III | A61B 17/0401 403/267 |
| 2015/0335320 A1* | 11/2015 | Keating | A61B 17/0401 606/144 |
| 2015/0352352 A1* | 12/2015 | Soltis | A61N 1/0558 607/116 |
| 2016/0256254 A1* | 9/2016 | Kucklick | A61F 2/0063 |
| 2016/0262780 A1* | 9/2016 | Kucklick | A61M 39/0606 |
| 2017/0172562 A1* | 6/2017 | Lombardo | A61B 17/0401 |
| 2017/0209136 A1* | 7/2017 | Sengun | A61B 17/0401 |
| 2017/0281229 A1* | 10/2017 | Hess | A61B 17/0218 |
| 2017/0360566 A1* | 12/2017 | Sikora | A61F 2/30734 |
| 2018/0070938 A1* | 3/2018 | Sauer | A61B 17/3417 |
| 2018/0249998 A1* | 9/2018 | Chavan | A61B 17/0487 |
| 2018/0263755 A1* | 9/2018 | Adams | A61F 2/0811 |

\* cited by examiner

SURGICAL PORT FOR STAY SUTURES

RELATED APPLICATIONS

This application claims priority to U.S. Provisional Patent Application No. 62/351,567 filed Jun. 17, 2016 and entitled, "SURGICAL PORT FOR STAY SUTURES". The entire 62/351,567 application is hereby incorporated by reference in its entirety.

FIELD

The claimed invention relates to surgical devices, and more specifically to surgical ports.

BACKGROUND

Laparoscopic, endoscopic, and other types of minimally invasive surgical procedures often rely on percutaneous introduction of surgical instruments into an internal region of a patient where the surgical procedure is to be performed. As part of many minimally invasive surgical procedures, stay sutures may be placed in various tissue and then tensioned either to pull the tissue out of the way or to move the tissue to a more convenient position for the surgeon to reach through a minimally invasive incision. Surgeons continue to find it desirable to utilize smaller and smaller access incisions in order to minimize trauma and reduce patient recovery times. In some situations, the minimally invasive access incision may only allow the surgeon to either set up the stay sutures or perform the ensuing surgical procedure, but does not allow for easy adjustment of the stay sutures once the ensuing surgical procedure is underway. Therefore, it would be desirable to have an improved device for routing the stay sutures separately from a main surgical access point while enabling convenient adjustment of the stay suture tensions.

SUMMARY

A surgical port is disclosed. The surgical port has a multi-level flange defining one or more suture channels therethrough. Adjacent levels of the multi-level flange are configured to pinch one or more sutures placed therebetween. The surgical port also has a cannular frame defining one or more cannular channels in communication with the one or more suture channels.

Another surgical port is disclosed. The surgical port has a multi-level flange defining three suture channels oriented in a triangular pattern therethrough. Adjacent levels of the multi-level flange are configured to pinch one or more sutures placed therebetween. The surgical port also has a cannular frame defining one or more cannular channels in communication with the one or more suture channels. The surgical port further has one or more suture outlets to couple at least one of the one or more suture channels to at least one of the adjacent levels of the multi-level flange.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 1A:
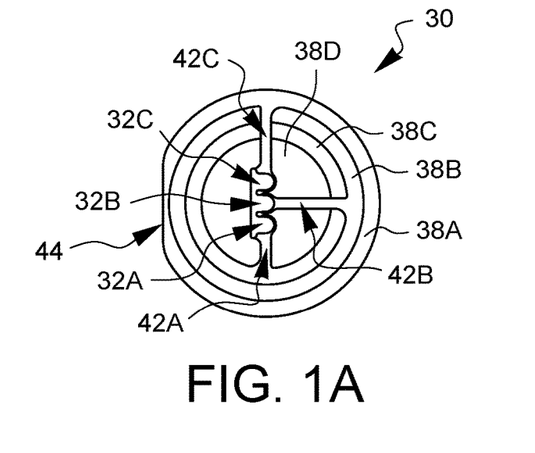
FIG. 1A is a top elevational view of one embodiment of a multi-level flange, viewed from a first top-view orientation.
Figure 1B:
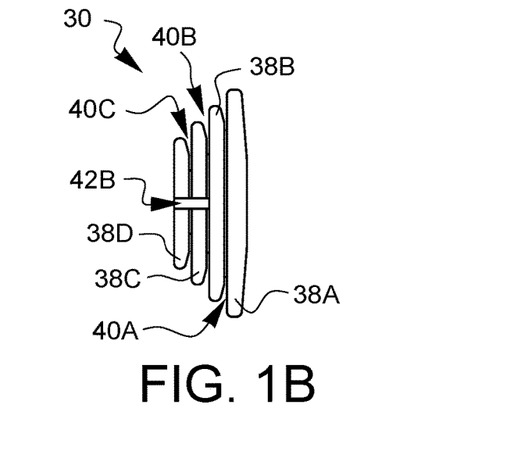
FIG. 1B is a side elevational view of the multi-level flange of FIG. 1A when taken from the right side as compared to the orientation of FIG. 1A.
Figure 1C:
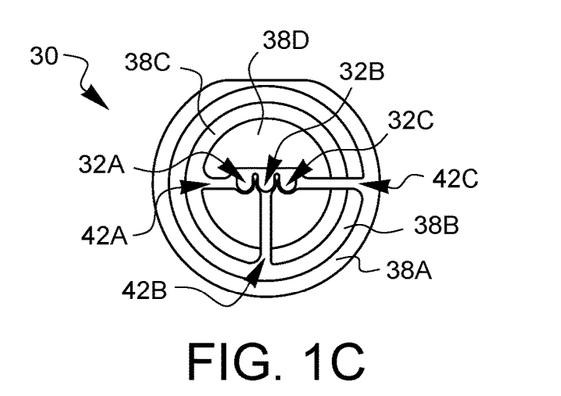
FIG. 1C is a top elevational view of the multi-level flange of FIG. 1A, viewed from a second top-view orientation that is rotated ninety degrees clockwise as compared to FIG. 1A.
Figure 1D:
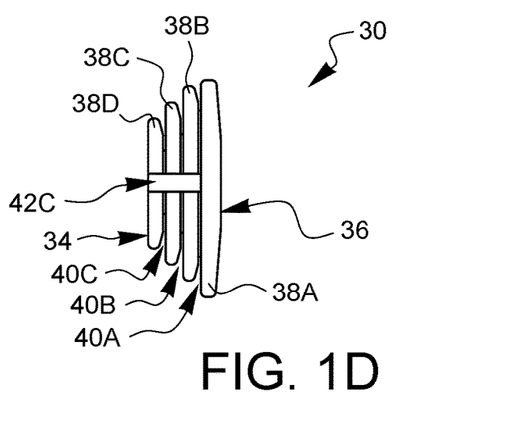
FIG. 1D is a side elevational view of the multi-level flange of FIG. 1C when taken from the right side as compared to the orientation of FIG. 1C.
Figure 2:
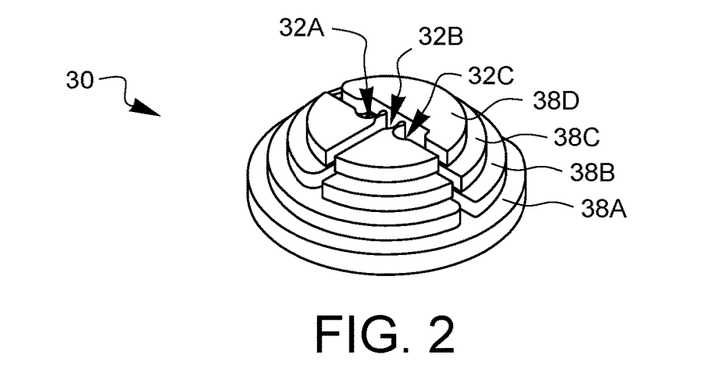
FIG. 2 is a perspective view of the multi-level flange of FIGS. 1A-1D.

FIG. 1A is a top view of a multi-level flange 30 in a first top-view orientation. FIG. 1B is a right side view of the multi-level flange 30 based on the related top-view orientation of FIG. 1A. FIG. 1C is a top view of the multi-level flange 30 in a second top-view orientation. This second top-view orientation is turned ninety degrees clockwise relative to the view of FIG. 1A. FIG. 1D is a right side view of the multi-level flange 30 based on the related top-view orientation of FIG. 1C. FIG. 2 is a front-right-top perspective view of the multi-level flange 30.

In this embodiment, the multi-level flange 30 has first, second, and third suture channels 32A, 32B, 32C formed therethrough, passing from a top side 34 of the multi-level flange 30 to a bottom side 36 of the multi-level flange 30. In this embodiment, the multi-level flange 30 has four levels 38A, 38B, 38C, and 38D. This creates three pairs of adjacent levels: a first pair between the first flange level 38A and the second flange level 38B; a second pair between the second flange level 38B and the third flange level 38C; and a third pair between the third flange level 38C and the fourth flange level 38D. Each pair of adjacent levels of the multi-level flange 30 are configured to pinch one or more sutures placed therebetween. The side views of FIGS. 1B and 1D illustrate the spacings 40A, 40B, and 40C between the respective adjacent levels 38A, 38B; 38B, 38C; and 38C, 38D. In this embodiment, some portions of the flanges 38A, 38B, 38C, 38D are tapered to help create a narrowing channel in the spaces 40A, 40B, 40C where a suture may be pinched.

The multi-level flange 30 has a first suture outlet 42A which couples the first suture channel 32A to the spacing 40C between the adjacent flange levels 38C, 38D. Similarly, the multi-level flange 30 has a second suture outlet 42B which couples the second suture channel 32B to the spacing 40B between the adjacent flange levels 38B, 38C. Similarly, the multi-level flange 30 has a third suture outlet 42C which couples the third suture channel 32C to the spacing 40A between adjacent flange levels 38A, 38B. The suture outlets 42A, 42B, 42C may provide more convenient routings for sutures that have been passed up through the suture channels 32A, 32B, 32C to be brought into contact with desired areas between flange levels so that they can then be pinched and held between an adjacent pair of levels. Other embodiments may not have suture outlets.

In this embodiment, the suture channels 32A, 32B, 32C are oriented in a substantially straight line, but in other embodiments, the suture channels could be spaced or oriented differently. Similarly, there could be more or fewer suture channels. In this embodiment, the suture channels 32A, 32B, 32C are substantially round and are in communication with each other, but in other embodiments, one or more of the suture channels could be completely separate from the other suture channels. Similarly, in other embodiments, one or more of the suture channels could have a shape that is not substantially round (when viewed from the top), for example, but not limited to, a round, elliptical, square, rectangular, triangular, or polygonal shape.

The flanges 38A, 38B, 38C, 38D are substantially round (when viewed from the top). Flange 38A has a flat side 44 to its otherwise substantially round shape. As will be discussed later in this specification, the multi-level flange 30 will be part of a surgical port that also includes a cannular frame. The flat side 44 of the flange 38A can help to prevent the surgical port from rolling away. The flat side 44 can also serve as a reference point for alignment of a pointed tip on some embodiments of a cannular frame, as will be discussed later in this specification.

In this embodiment, the flange levels 38A, 38B, 38C, 38D are progressively smaller, but in other embodiments, different relative sizes could be used, or even similar sizes could be used. In this embodiment, the number of flanges 38A, 38B, 38C, 38D totals one more than the number of suture channels 32A, 32B, 32C. In other embodiments, there could be different relative numbers of flanges to suture channels.

Figure 3A:
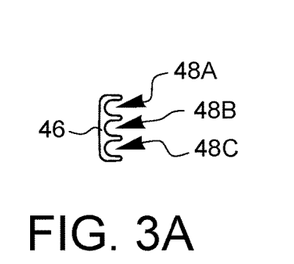
FIG. 3A is a top elevational view of one embodiment of a cannular frame in a third top-view orientation that happens to be one hundred eighty degrees from the first top-view orientation.
Figure 3B:
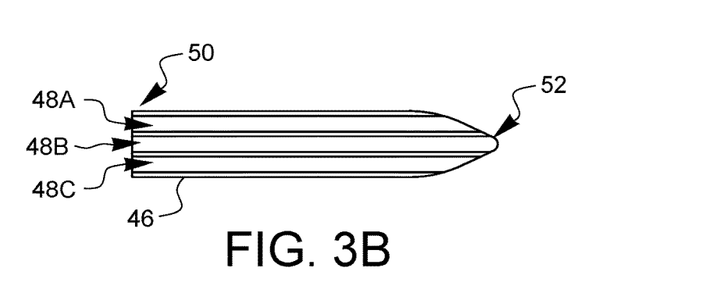
FIG. 3B is a side elevational view of the cannular frame of FIG. 3A when taken from the right side as compared to the orientation of FIG. 3A.
Figure 4A:
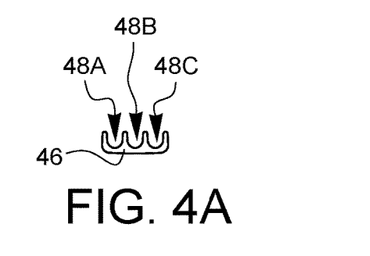
FIG. 4A is a top elevational view of the cannular frame of FIG. 3A, viewed from the first top-view orientation.
Figure 4B:
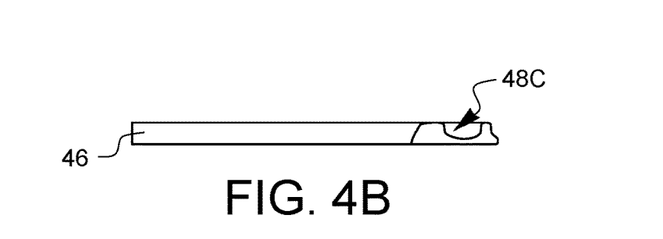
FIG. 4B is a side elevational view of the cannular frame of FIG. 4A when taken from the right side as compared to the orientation of FIG. 4A.

FIG. 3A is a top view of a cannular frame 46 in a first top-view orientation (that happens to be 180 degrees off from the top-view orientation of FIG. 1A). FIG. 3B is a right side view of the cannular frame 46 based on the related top-view orientation of FIG. 3A. FIG. 4A is a top view of the cannular frame 46 in a second top-view orientation. This second top-view orientation is turned ninety degrees counter-clockwise relative to the view of FIG. 3A (and happens to be the same orientation as FIG. 1C). FIG. 4B is a right side view of the cannular frame 46 based on the related top-view orientation in FIG. 4A.

In this embodiment, the cannular frame 46 has first, second, and third cannular channels 48A, 48B, 48C. As will be shown in later portions of this specification, the top end 50 of the cannular frame 46 will be coupled to the bottom side 36 of the multi-level flange 30 such that the cannular channels 48A, 48B, 48C align with the suture channels 32A, 32B, 32C in the multi-level flange 30. In this embodiment, the cannular frame 46 has a pointed tip 52. The pointed tip 52 may help the cannular frame 46 to pierce tissue. Other embodiments may have a cannular frame 46 that does not have a pointed tip.

Figure 5A:
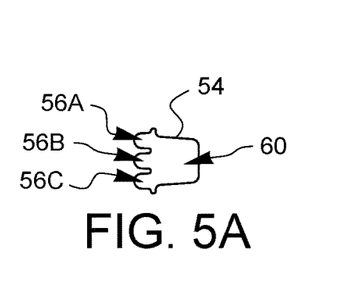
FIG. 5A is a top elevational view of one embodiment of an obturator, viewed from the third top-view orientation.
Figure 5B:
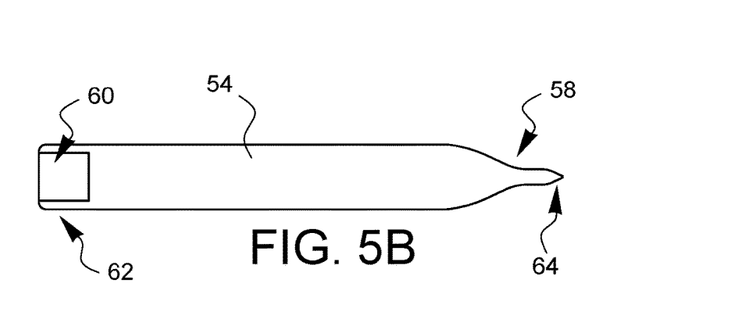
FIG. 5B is a side elevational view of the obturator of FIG. 5A when taken from the right side as compared to the orientation of FIG. 5A.
Figure 6A:
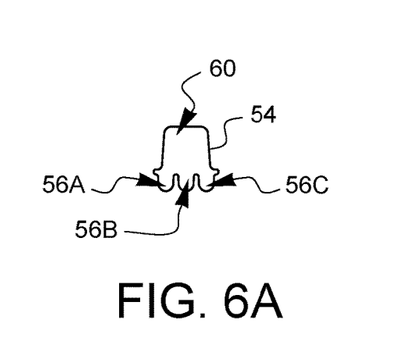
FIG. 6A is a top-elevational view of the obturator of FIG. 5A, viewed from the first top view orientation.
Figure 6B:
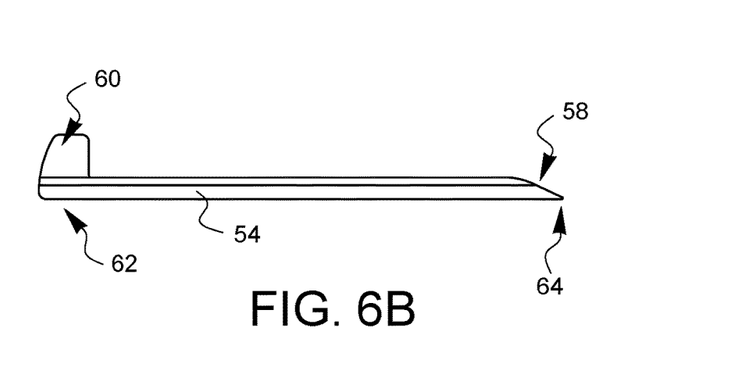
FIG. 6B is a side elevational view of the obturator of FIG. 6A when taken from the right side as compared to the orientation of FIG. 6A.

FIG. 5A is a top view of an obturator 54 in a first top-view orientation (that happens to be 180 degrees off from the top-view orientation of FIG. 1A and the same as the top-view orientation of FIG. 3A). FIG. 3B is a right side view of the obturator 54 based on the related top-view orientation of FIG. 5A. FIG. 6A is a top view of the obturator 54 in a second top-view orientation. This second top-view orientation is turned ninety degrees counter-clockwise relative to the view of FIG. 5A (and happens to be the same orientation as FIG. 1C and FIG. 4A). FIG. 6B is a right side view of the obturator 54 based on the related top-view orientation in FIG. 6A.

The obturator 54 has ridges 56A, 56B, 56C which are configured to slide within the suture channels 32A, 32B, 32C and the cannular channels 48A, 48B, 48C of an assembled surgical port made up of the multi-level flange 30 and the cannular frame 46. A leading end 58 of the obturator 54 is insertable in the suture channels 32A, 32B, 32C from the top side 34 of the multi-level flange 30. A stop 60 on a trailing end 62 of the obturator 54 prevents the obturator 54 from being able to pass all of the way through the suture channels 32A, 32B, 32C, thereby preventing it from being able to fall into a patient. The stop 60 may also act as a convenient handle for grasping and moving the obturator 54. In this embodiment, the obturator 54 also has a pointed tip 64. If the obturator 54 is only partially pushed into the suture channels 32A, 32B, 32C and the cannular channels 48A, 48B, 48C, then the pointed tip 64 of the obturator 54 may not be protruding past the end of the cannular frame 46. When the pointed tip 64 of the obturator 54 is desired to be exposed, the obturator 54 may be pressed all of the way in.

Figure 7:
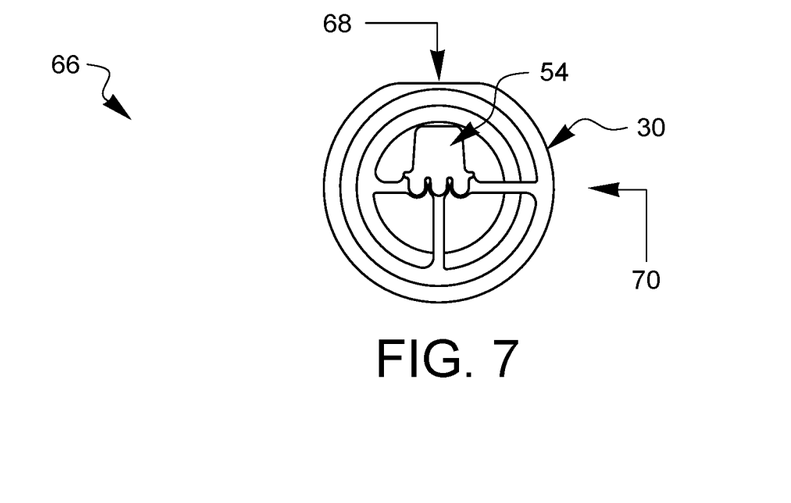
FIG. 7 is a top elevational view of one embodiment of an assembled surgical port, viewed from the second top view orientation.
Figure 8A:
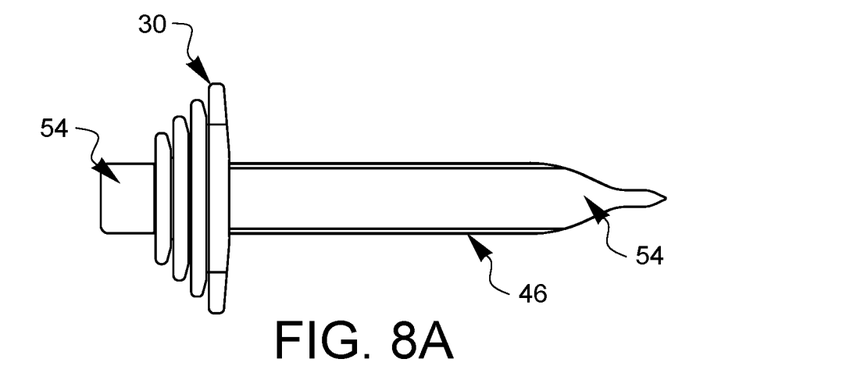
FIG. 8A is a side elevational view of the surgical port of FIG. 7 looking at the port from FIG. 7's vantage point 68.
Figure 8B:
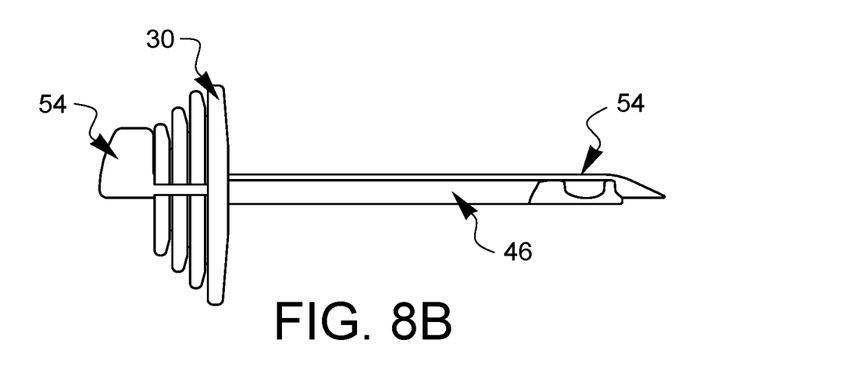
FIG. 8B is a side elevational view of the surgical port of FIG. 7 looking at the port from FIG. 7's vantage point 70.

FIG. 7 is a top view of an assembled surgical port 66 having multi-level flange 30, a cannular frame 46 coupled to the multi-level flange 30 (but not visible in this view) and an obturator 54 slid all of the way into the suture channels and the cannular channels of the port 66. FIG. 8A is a side view of the surgical port 66 of FIG. 7, looking at the port from FIG. 7's vantage point 68. FIG. 8B is another side view of the surgical port 66 of FIG. 7, looking at the port from FIG. 7's vantage point 70.

Figure 9A:
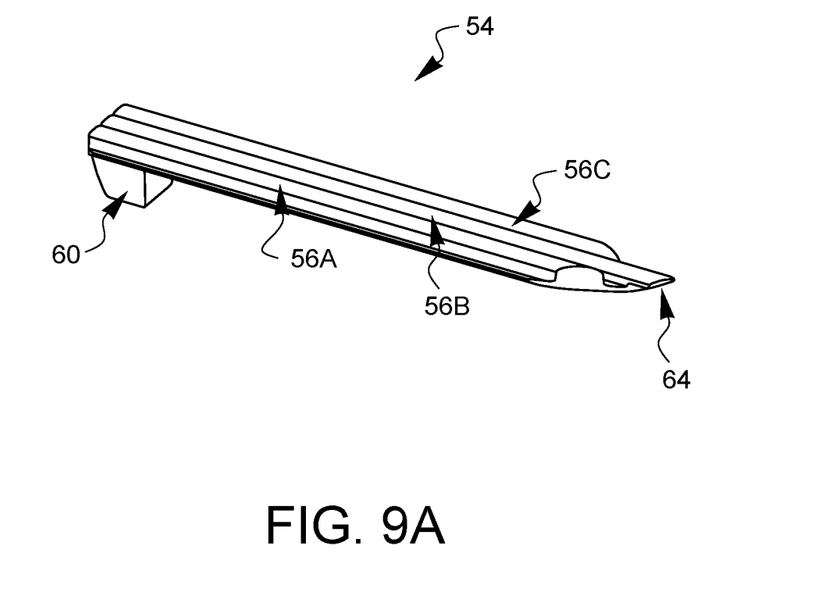
FIG. 9A is a perspective view of the obturator of FIG. 5A which better shows the ridges of the obturator and the pointed tip.
Figure 9B:
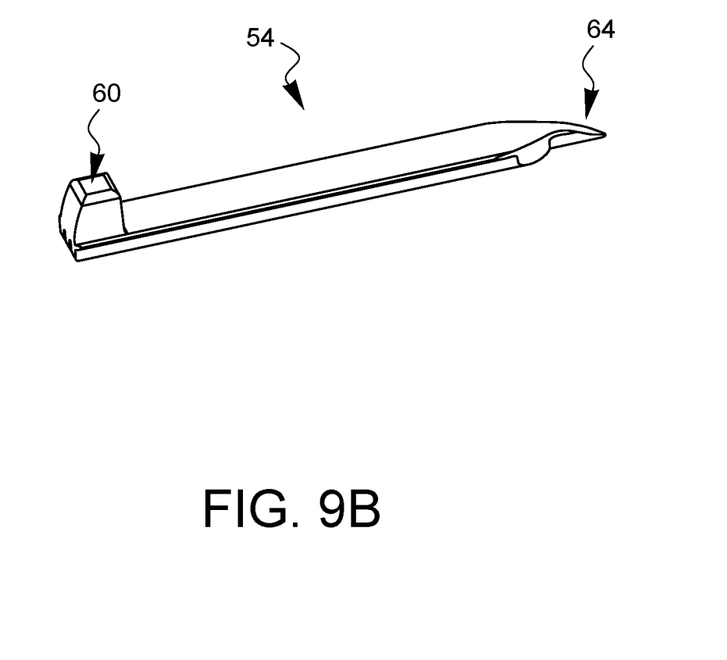
FIG. 9B is another perspective view of the obturator of FIG. 9A from the opposite side which shows the stop more clearly.

FIG. 9A is a perspective view of the obturator 54, to better show the ridges 56A, 56B, 56C, the stop 60, and the pointed tip 64. FIG. 9B is another perspective view of the obturator 54 from the opposite side, where the stop 60 can be seen more clearly.

Figure 10A:
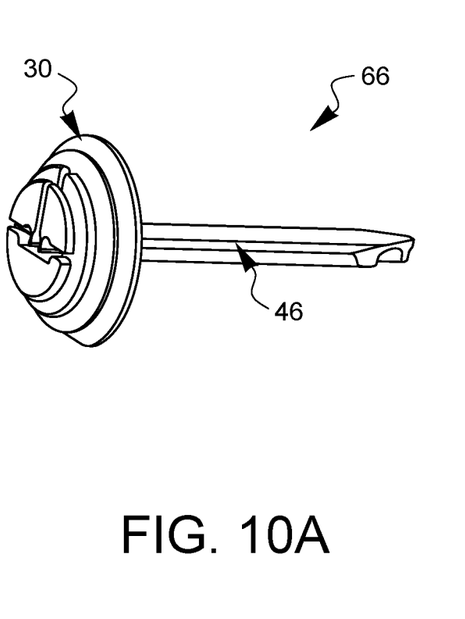
FIG. 10A is a perspective view of the surgical port in a configuration which does not have an obturator installed.
Figure 10B:
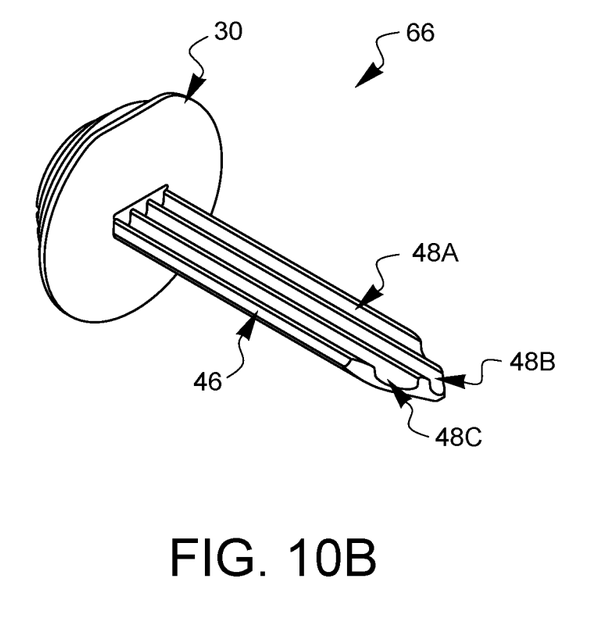
FIG. 10B is a different perspective view of the surgical port of FIG. 10A in which the cannular channels can be seen more clearly.

FIG. 10A is a perspective view of the surgical port 66 in a configuration that does not have an obturator installed. The multi-level flange 30 and the cannular frame 46 may be seen. FIG. 10B is another perspective view of the surgical port 66 from an opposite side and vantage point. In FIG. 10B, the cannular channels 48A, 48B, 48C can be seen more clearly.

Figure 11A:
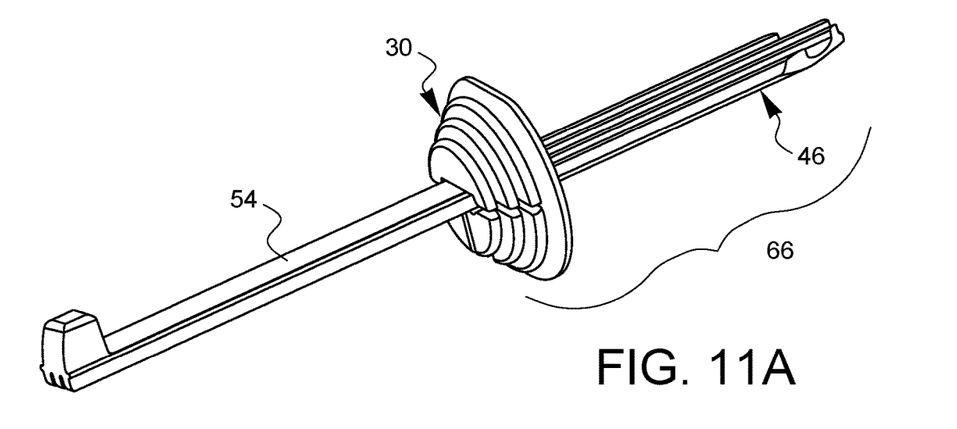
FIG. 11A is a perspective view of a surgical port having an obturator just beginning to be inserted therein.
Figure 11B:
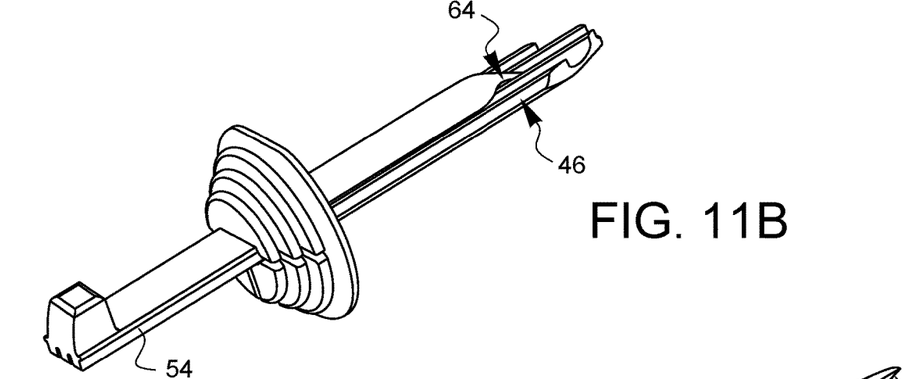
FIG. 11B is a perspective view of the surgical port of FIG. 11B where the obturator is partly installed.
Figure 11C:
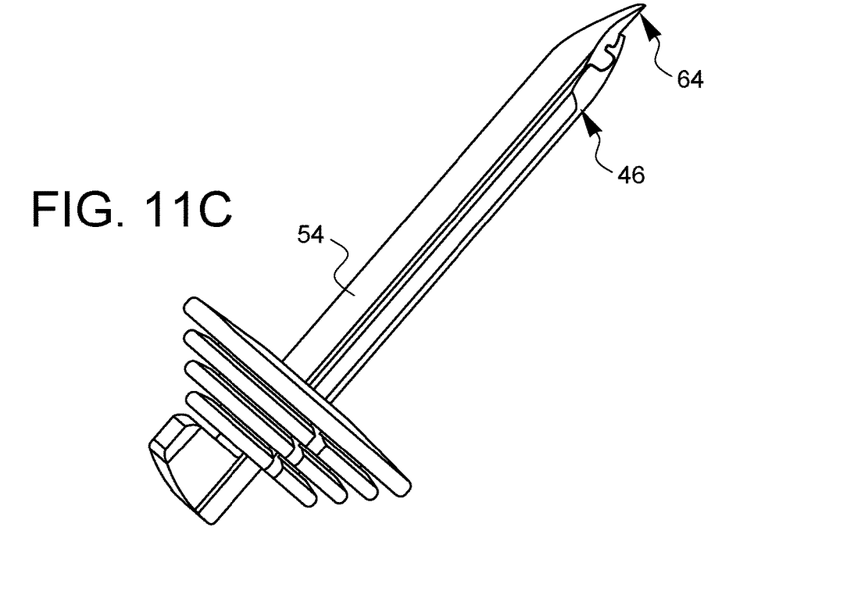
FIG. 11C is a perspective view of the surgical port of FIG. 11C where the obturator is fully installed.
Figure 12A:
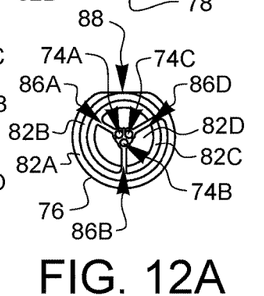
FIGS. 12A, 12B, 12C, 12D, 12E, and 12F are top, left, right, bottom, rear, and front elevational views, respectively, of another embodiment of a surgical port.
Figure 12B:
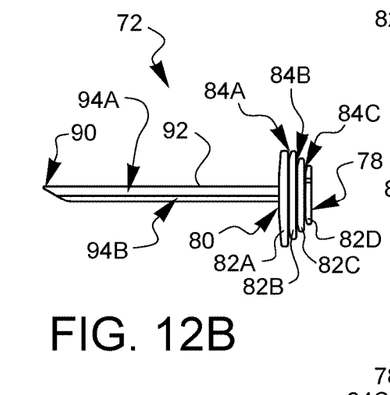
Figures 12C, 12D:
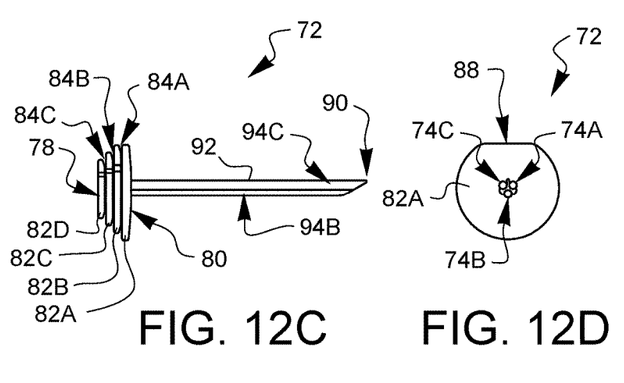
Figure 12E:
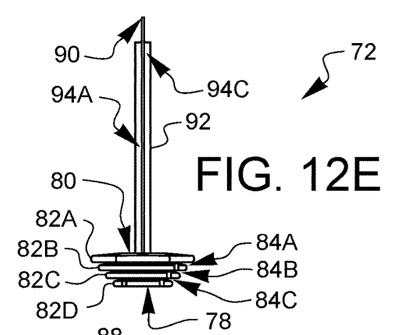
Figure 12F:
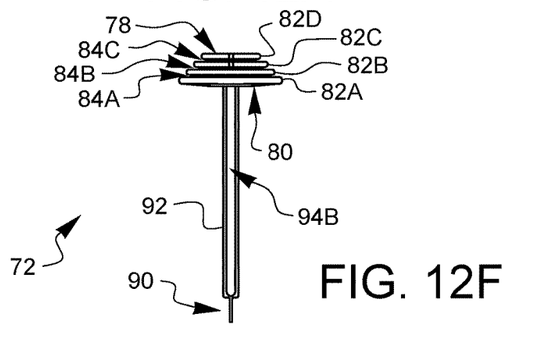

FIGS. 11A-11C are perspective views of a surgical port 66 having an obturator 54 just beginning to be inserted, partly installed so the obturator point 64 is not protruding from the cannular frame 46, and then fully installed so the obturator point 64 has extended past the cannular frame 46.

FIGS. 12A, 12B, 12C, 12D, 12E, and 12F are top, left, right, bottom, rear, and front elevational views, respectively, of another embodiment of a surgical port 72. While this embodiment is similar to the earlier embodiment, it has suture channels 74A, 74B, 74C which are oriented in a triangular pattern. The first, second, and third suture channels 74A, 74B, 74C are formed through a multi-level flange 76, passing from a top side 78 of the multi-level flange 76 to a bottom side 78 of the multi-level flange 76. In this embodiment, the multi-level flange 76 has four levels 82A, 82B, 82C, and 82D. This creates three pairs of adjacent levels: a first pair between the first flange level 82A and the second flange level 82B; a second pair between the second flange level 82B and the third flange level 82C; and a third pair between the third flange level 82C and the fourth flange level 82D. Each pair of adjacent levels of the multi-level flange 76 are configured to pinch one or more sutures placed therebetween. In this embodiment, some portions of the flanges 82A, 82B, 82C, 82D are tapered to help create a narrowing channel in the spaces 84A, 84B, 84C where a suture may be pinched.

The multi-level flange 76 has a first suture outlet 86A which couples the first suture channel 74A to the spacing 84C between the adjacent flange levels 82C, 82D. Similarly, the multi-level flange 76 has a second suture outlet 86B which couples the second suture channel 74B to the spacing 84B between the adjacent flange levels 82B, 82C. Similarly, the multi-level flange 76 has a third suture outlet 86C which couples the third suture channel 74C to the spacing 84A between adjacent flange levels 82A, 82B. The suture outlets 86A, 86B, 86C may provide more convenient routings for sutures that have been passed up through the suture channels 74A, 74B, 74C to be brought into contact with desired areas between flange levels so that they can then be pinched and held between an adjacent pair of levels. Other embodiments may not have suture outlets. Furthermore, it should be noted that the suture outlets 86A, 86B, 86C are spaced approximately one-hundred twenty degrees apart in this embodiment. Suture outlets in other embodiments could have different spacings.

In other embodiments, there could be more or fewer than three suture channels 74A, 74B, 74C. In this embodiment, the suture channels 74A, 74B, 74C are separate from each other, but in other embodiments, two or more of the suture channels could be in communication with each other. Similarly, in other embodiments, one or more of the suture channels could have a shape that is not substantially round (when viewed from the top), for example, but not limited to, a round, elliptical, square, rectangular, triangular, or polygonal shape.

In this embodiment, the flange levels 82A, 82B, 82C, 82D are progressively smaller, but in other embodiments, different relative sizes could be used, or even similar sizes could be used. In this embodiment, the number of flanges 82A, 82B, 82C, 82D totals one more than the number of suture channels 74A, 74B, 74C. In other embodiments, there could be different relative numbers of flanges to suture channels.

The flanges 82A, 82B, 82C, 82D are substantially round (when viewed from the top). Flange 82A has a flat side 88 to its otherwise substantially round shape. The flat side 88 of the flange 82A can help to prevent the surgical port 72 from rolling away. The flat side 88 can also serve as a reference point for alignment of a pointed tip 90 on the cannular frame 92. The cannular frame 92 has first, second, and third cannular channels 94A, 94B, 94C which are in alignment with respective suture channels 74A, 74B, 74C.

Figure 13:
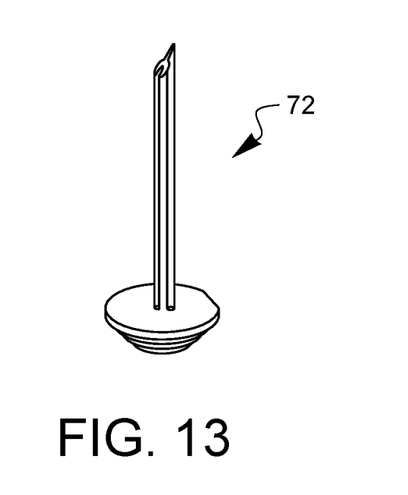
FIGS. 13, 14A, and 14B are different perspective views of the surgical port of FIGS. 12A-12F.
Figure 14A:
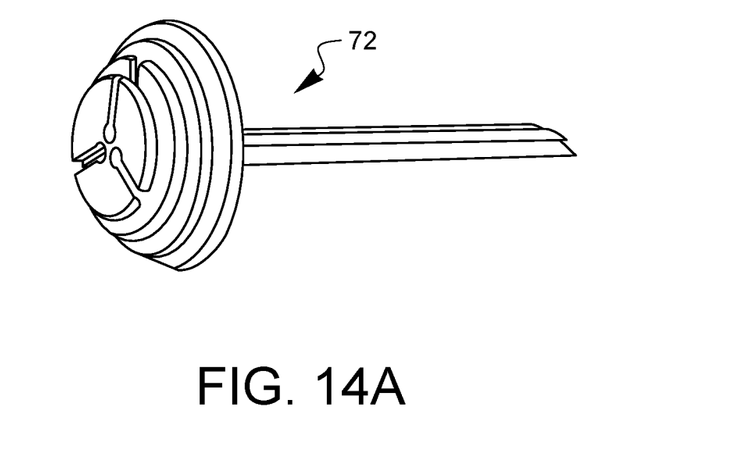
Figure 14B:
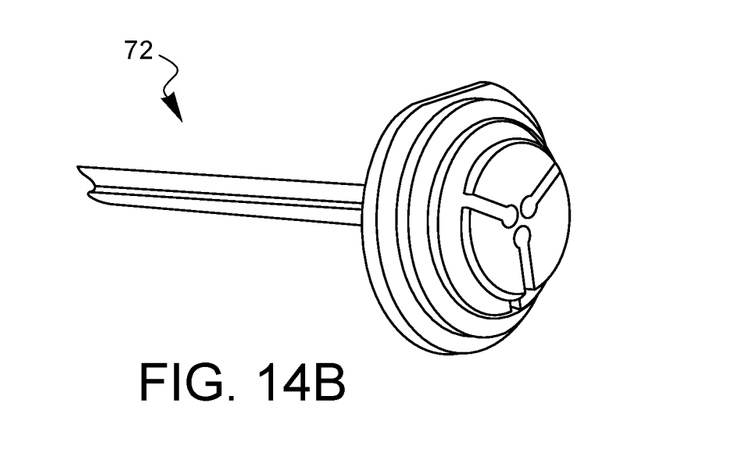

FIGS. 13, 14A, and 14B are different perspective views of the surgical port 72 of FIGS. 12A-12F.

Figure 15A:
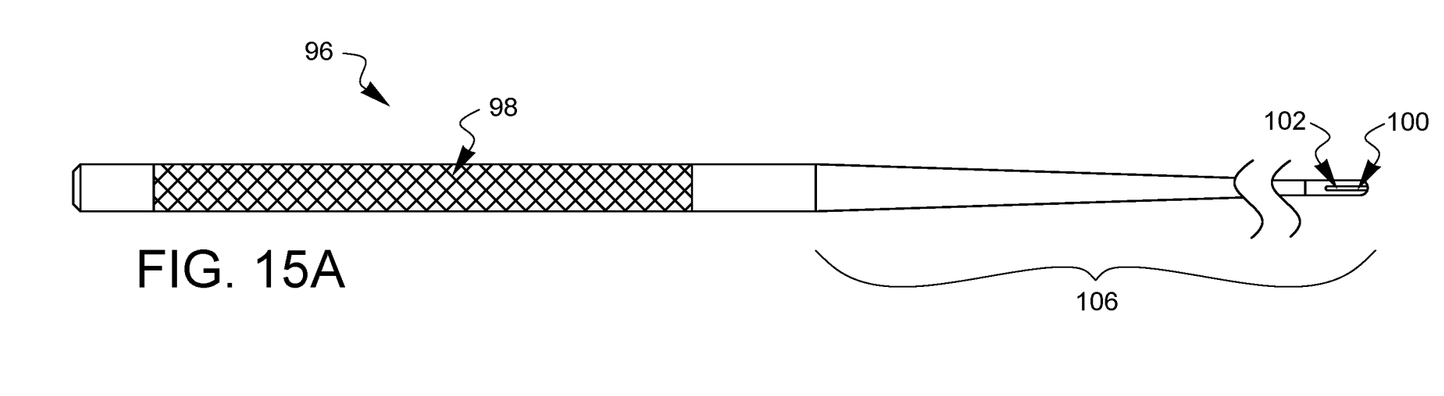
FIGS. 15A and 15B are enlarged top and side elevational views, respectively, of one embodiment of a suture snare for use with a surgical port.
Figure 15B:
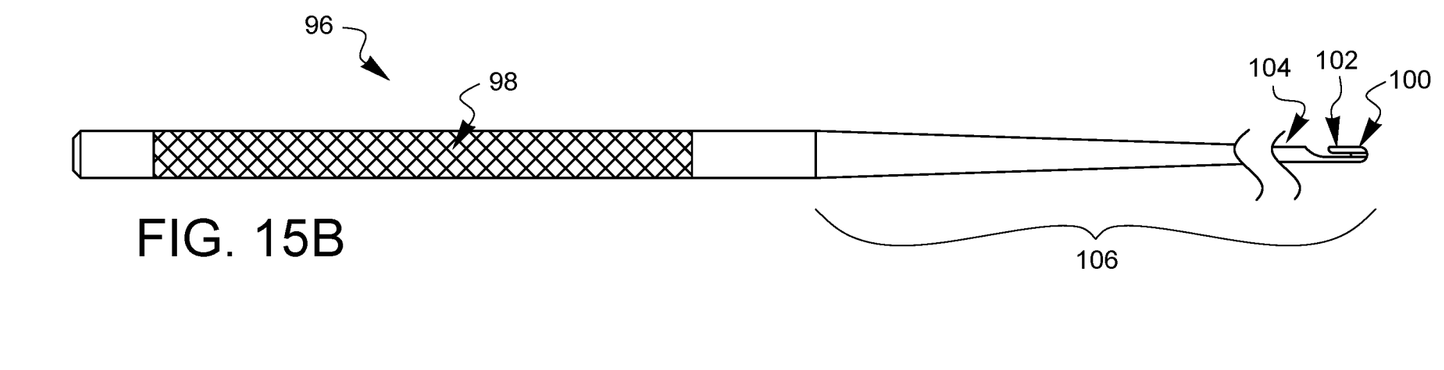

FIGS. 15A and 15B are enlarged top and side elevational views, respectively, of one embodiment of a suture snare 96. The snare 96 has a handle 98 and a hook 100. Since the snare 96 tapers from the larger handle 98 to the smaller hook 100, the trailing edge 102 of the hook 100 does not extend past the diameter of the taper 104 near the hook 102. This helps to keep the hook 100 from getting caught on tissue. The snare 96 is sized so that at least the distal portion 106 can pass through one of the suture channels of the suture port. The snare 96 may be used to capture a suture within a patient and draw the suture ends back out through one of the suture channels of the suture port.

Various advantages of a surgical port for stay sutures have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:
1. A surgical port, comprising:
a multi-level flange defining one or more suture channels therethrough, and wherein:
adjacent levels of the multi-level flange are configured to pinch one or more sutures placed therebetween;
each of the levels of the multi-level flange lie in non-intersecting planes; and
each of the adjacent levels comprise spaces therebetween;
each of the spaces comprise a tapered channel between adjacent levels; and a cannular frame defining one or more cannular channels in communication with the one or more suture channels.

2. The surgical port of claim 1, further comprising one or more suture outlets to couple at least one of the one or more suture channels to at least one of the adjacent levels of the multi-level flange.

3. The surgical port of claim 1, wherein the one or more suture channels are oriented in a straight line.

4. The surgical port of claim 1, wherein the one or more suture channels comprise three suture channels oriented in a triangular pattern.

5. The surgical port of claim 1, wherein at least one of the one or more suture channels have a circular shape.

6. The surgical port of claim 1, wherein at least one level of the multi-level flange comprises a flat side.

7. The surgical port of claim 1, wherein at least one level of the multi-level flange comprises a shape selected from the group consisting of round, elliptical, square, rectangular, triangular, and polygonal.

8. The surgical port of claim 1, wherein the cannular frame comprises a pointed tip.

9. The surgical port of claim 1, further comprising an obturator configured to slide within the suture channels and the cannular channels of the surgical port.

10. The surgical port of claim 9, wherein the obturator is removable from the suture channels and the cannular channels.

11. The surgical port of claim 9, wherein the obturator comprises a pointed tip.

12. A surgical port, comprising:
   a multi-level flange defining three suture channels oriented in a triangular pattern therethrough, and wherein:
      adjacent levels of the multi-level flange are configured to pinch one or more sutures placed therebetween; and
      each of the levels of the multi-level flange lie in non-intersecting planes;
      each of the adjacent levels comprise spaces therebetween;
      each of the spaces comprise a tapered channel between adjacent levels; and
   a cannular frame defining one or more cannular channels in communication with the one or more suture channels; and
   one or more suture outlets to couple at least one of the one or more suture channels to at least one of the adjacent levels of the multi-level flange.

* * * * *